United States Patent [19]

Fischer, deceased

[11] Patent Number: 4,690,706

[45] Date of Patent: Sep. 1, 1987

[54] HERBICIDE

[75] Inventor: Adolf Fischer, deceased, late of Mutterstadt, Fed. Rep. of Germany, by Caecilia Emma Fischer, legal representative

[73] Assignee: BASF Aktiengesellschaft, Ludwigshafen, Fed. Rep. of Germany

[21] Appl. No.: 321,727

[22] Filed: Nov. 16, 1981

Related U.S. Application Data

[63] Continuation-in-part of Ser. No. 257,867, Apr. 27, 1981, abandoned, which is a continuation of Ser. No. 98,860, Nov. 30, 1979, abandoned, which is a continuation of Ser. No. 732,899, Oct. 15, 1976, abandoned, which is a continuation of Ser. No. 453,305, Mar. 21, 1974, abandoned.

[30] Foreign Application Priority Data

Apr. 17, 1973 [DE] Fed. Rep. of Germany ....... 2319364

[51] Int. Cl.$^4$ .............................. A01N 43/88
[52] U.S. Cl. .......................... 71/91; 71/108; 71/116
[58] Field of Search ............................. 71/91

[56] References Cited

PUBLICATIONS

Letraud et al, Chem. Abstr., vol. 79, (1973), No. 112286k.
Defloor, Chem. Abstr., vol. 77, (1972), No. 44194k.
Bartoska, Chem. Abstr., vol. 81, (1974), No. 146720d.
W. T. Thomson, Agricultural Chemicals-Book II, Herbicides, (1964), pp. 12, 15.

*Primary Examiner*—Catherine L. Mills
*Attorney, Agent, or Firm*—Keil & Weinkauf

[57] ABSTRACT

New and valuable herbicidal composition based on benzothiadiazinone dioxide derivatives and phenoxybutyric acid derivatives.

6 Claims, No Drawings

HERBICIDE

The present invention is a continuation-in-part of application Ser. No. 257,867, filed Apr. 27, 1981, abandoned, which is a continuation of application Ser. No. 098,860, filed Nov. 30, 1979, abandoned, which is a continuation of application Ser. No. 732,899, filed Oct. 15, 1976, abandoned, which in turn is a continuation of application Ser. No. 453,305, filed Mar. 21, 1974, now abandoned.

The present invention relates to herbicides containing compositions of various active ingredients.

It is known to use phenoxycarboxylic acid derivatives and benzothiadiazinone dioxides as postemergence selective herbicides in various crops. However, their action is not always satisfactory.

I have now found that a composition of a compound of the formula

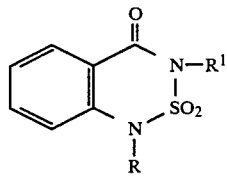 (a)

where R denotes hydrogen or a salt such as an ammonium, sodium, potassium, calcium, magnesium, ethylamine, dimethylamine, diethylamine, ethanolamine, diethanolamine or dimethylethanolamine salt, $R^1$ denotes methyl, ethyl, propyl, isopropyl, sec-butyl, n-butyl or isobutyl, and a compound of the formula

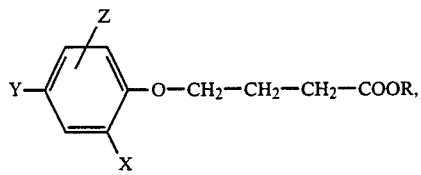 (b)

where X denotes hydrogen, chloro or methyl, Y denotes hydrogen, chloro or methyl, Z denotes hydrogen, chloro or methyl, and R denotes alkyl, hydrogen, or a salt of a carboxylic acid, has a good herbicidal action.

The ratio of a:b may be varied at will; it is however preferred to employ from 0.1 to 10 parts by weight of a to from 0.1 to 10 parts by weight of b. Application rates are from 0.1 to 15, preferably from 0.1 to 5, kg per hectare.

The compositions have a selective action in cereals, rice, Indian corn, and other crops but are particularly useful on leguminosae, e.g. peas, clover, soybeans and peanuts. The compositions are effective in destroying a wide variety of weeds but are particularly effective in controlling Ipomoea spp. (morning glory), *Xanthium pensylvanicum* (cocklebur) and *Sida spinosa* (prickly sida).

Application may be effected for instance in the form of directly sprayable solutions, powders, suspensions, dispersions, emulsions, oil dispersions, pastes, dusts, or granules by spraying, atomizing, dusting, broadcasting or watering. The form of application depends entirely on the purpose for which the agents are being used; in any case it should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils and oils of vegetable or mineral origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated napthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

The formulations contain from 0.1 to 95, and preferably 0.5 to 90%, by weight of active ingredient.

There may be added to the compositions or individual active ingredients (if desired, immediately before use) oils of various types, herbicides, fungicides, nematocides, insecticides, bactericides, trace elements, fertilizers, antifoams (e.g., silicones), growth regulators, antidotes and other herbicidally effective compounds.

EXAMPLE 1

In the greenhouse, various plants were treated at a growth height of from 2 to 15 cm with the following amounts of the following individual active ingredients and compositions thereof as dispersions or dusts.

I  3-isopropyl-2,1,3-benzothiadiazinone-(4)-2,2-dioxide, sodium salt; 0.1, 0.25, 0.5, 0.75, 1.0, 1.1, 1.5, 2 and 3 kg per hectare;

II  3-isopropyl-2,1,3-benzothiadiazinone-(4)-2,2-dioxide; 0.1, 0.25, 0.5, 0.75, 1.0, 1.1, 1.5, 2 and 3 kg per hectare;

III γ-(2-methyl-4-chlorophenoxy)-butyric acid, sodium salt, 0.1, 0.25, 0.5, 0.75, 1.0, 1.1, 1.5, 2 and 3 kg per hectare;

IV γ-(4-chlorophenoxy)-butyric acid, sodium salt, 0.1, 0.25, 0.5, 0.75, 1.0, 1.1, 1.5, 2 and 3 kg per hectare;

I+III: 0.1+1, 1+0.1, 0.25+0.25, 0.25+0.75, 0.75+0.25, 0.5+0.5, 2+1, 1+2, 1+1 and 1.5+1.5 kg per hectare;

I+IV: 0.1+1, 1+0.1, 0.25+0.25, 0.25+0.75, 0.75+0.25, 0.5+0.5, 2+1, 1+2, 1+1 and 1.5+1.5 kg per hectare;

II+III: 0.1+1, 1+0.1, 0.25+0.25, 0.25+0.75, 0.75+0.25, 0.5+0.5, 2+1, 1+2, 1+1 and 1.5+1.5 kg per hectare.

After 10 to 17 days it was ascertained that the compositions had a better herbicidal action than their components, combined with the same good crop plant compatibility.

The results are given below:

the following individual active ingredients and compositions thereof as emulsions or pastes:

I 3-isopropyl-2,1,3-benzothiadiazinone-(4)-2,2-dioxide, dimethylamine salt, 0.25, 0.75, 1.25 and 1.5 kg per hectare;

II γ-(2,4,5-trichlorophenoxy)-butyric acid, dimethylamine salt, 0.25, 0.75, 1.25 and 1.5 kg per hectare;

III γ-(2,4-dichlorophenoxy)-crotonic acid, dimethylamine salt, 0.25, 0.75, 1.25 and 1.5 kg per hectare;

IV α-(4-chlorophenoxy)-propionic acid, dimethylamine salt, 0.25, 0.75, 1.25 and 1.5 kg per hectare;

V 2-chlorophenoxyacetic acid, dimethylamine salt, 0.25, 0.75, 1.25 and 1.5 kg per hectare;

VI 4-chlorophenoxyacetic acid, dimethylamine salt, 0.25, 0.75, 1.25 and 1.5 kg per hectare;

I+II: 0.25+1.25, 1.25+0.25, 0.75+0.75 kg per hectare;

I+III: 0.25+1.25, 1.25+0.25, 0.75+0.75 kg per hectare;

I+IV: 0.25+1.25, 1.25+0.25, 0.75+0.75 kg per hect-

| kg/ha | 0.1 | 0.25 | 0.5 | 0.75 | 1 | 1.1 | 1.5 | 2 | 3 | 0.1 | 0.25 | 0.5 | 0.75 | 1 | 1.1 | 1.5 | 2 | 3 |
|---|---|---|---|---|---|---|---|---|---|---|---|---|---|---|---|---|---|---|
| Active ingredient | I | | | | | | | | | II | | | | | | | | |
| Crop plants: | | | | | | | | | | | | | | | | | | |
| Medicago sativa | 0 | 0 | 0 | 0 | 0 | 0 | 0 | 0 | 5 | 0 | 0 | 0 | 0 | 0 | 0 | 0 | 0 | 5 |
| Pisum sativum | 0 | 0 | 0 | 0 | 0 | 0 | 0 | 0 | 0 | 0 | 0 | 0 | 0 | 0 | 0 | 0 | 0 | 0 |
| Trifolium spp. | 0 | 0 | 0 | 0 | 0 | 0 | 0 | 0 | 5 | 0 | 0 | 0 | 0 | 0 | 0 | 0 | 0 | 5 |
| Unwanted plants: | | | | | | | | | | | | | | | | | | |
| Galium aparine | 8 | 15 | 30 | 40 | 60 | 60 | 75 | 80 | 95 | 10 | 20 | 35 | 45 | 65 | 67 | 75 | 80 | 95 |
| Raphanus raphanistrum | 8 | 15 | 20 | 30 | 42 | 45 | 70 | 78 | 100 | 10 | 20 | 30 | 35 | 45 | 50 | 72 | 80 | 100 |
| Stellaria media | 3 | 10 | 20 | 30 | 55 | 57 | 70 | 80 | 94 | 10 | 25 | 30 | 40 | 60 | 60 | 70 | 75 | 95 |
| Active ingredient | III | | | | | | | | | IV | | | | | | | | |
| Medicago sativa | 0 | 0 | 0 | 0 | 0 | 0 | 0 | 0 | 5 | 0 | 0 | 0 | 0 | 0 | 0 | 0 | 0 | 5 |
| Pisum sativum | 0 | 0 | 0 | 0 | 0 | 0 | 0 | 0 | 5 | 0 | 0 | 0 | 0 | 0 | 0 | 0 | 0 | 0 |
| Trifolium spp. | 0 | 0 | 0 | 0 | 0 | 0 | 0 | 0 | 7 | 0 | 0 | 0 | 0 | 0 | 0 | 0 | 0 | 5 |
| Galium aparine | 2 | 5 | 8 | 10 | 12 | 15 | 20 | 30 | 48 | 0 | 3 | 8 | 10 | 13 | 17 | 20 | 25 | 35 |
| Raphanus raphanistrum | 3 | 8 | 10 | 15 | 18 | 20 | 26 | 45 | 60 | 5 | 10 | 14 | 17 | 20 | 23 | 28 | 40 | 50 |
| Stellaria media | 0 | 3 | 8 | 10 | 15 | 15 | 20 | 25 | 40 | 0 | 5 | 7 | 11 | 15 | 18 | 23 | 27 | 35 |

| kg/ha | 0.1 + 1 | 1 + 0.1 | 0.25 + 0.25 | 0.25 + 0.75 | 0.75 + 0.25 | 0.5 + 0.5 | 2 + 1 | 1 + 2 | 1 + 1 | 1.5 + 1.5 |
|---|---|---|---|---|---|---|---|---|---|---|
| Active ingredient | I + III | | | | | | | | | |
| Crop plants: | | | | | | | | | | |
| Medicago sativa | 0 | 0 | 0 | 0 | 0 | 0 | 0 | 0 | 0 | 0 |
| Pisum sativum | 0 | 0 | 0 | 0 | 0 | 0 | 0 | 0 | 0 | 0 |
| Trifolium spp. | 0 | 0 | 0 | 0 | 0 | 0 | 0 | 0 | 0 | 0 |
| | I + IV | | | | | | | | | |
| Medicago sativa | 0 | 0 | 0 | 0 | 0 | 0 | 0 | 0 | 0 | 0 |
| Pisum sativum | 0 | 0 | 0 | 0 | 0 | 0 | 0 | 0 | 0 | 0 |
| Trifolium spp. | 0 | 0 | 0 | 0 | 0 | 0 | 0 | 0 | 0 | 0 |
| | II + III | | | | | | | | | |
| Medicago sativa | 0 | 0 | 0 | 0 | 0 | 0 | 0 | 0 | 0 | 0 |
| Pisum sativum | 0 | 0 | 0 | 0 | 0 | 0 | 0 | 0 | 0 | 0 |
| Trifolium spp. | 0 | 0 | 0 | 0 | 0 | 0 | 0 | 0 | 0 | 0 |
| Active ingredient | I + III | | | | | | | | | |
| Unwanted plants: | | | | | | | | | | |
| Galium aparine | 60 | 93 | 57 | 64 | 80 | 78 | 100 | 100 | 97 | 100 |
| Raphanus raphanistrum | 70 | 87 | 60 | 72 | 76 | 70 | 100 | 100 | 90 | 100 |
| Stellaria media | 57 | 78 | 50 | 56 | 70 | 65 | 100 | 98 | 95 | 100 |
| | I + IV | | | | | | | | | |
| Galium aparine | 58 | 90 | 54 | 60 | 77 | 75 | 100 | 100 | 95 | 100 |
| Raphanus raphanistrum | 67 | 85 | 60 | 70 | 75 | 68 | 100 | 100 | 92 | 100 |
| Stellaria media | 55 | 75 | 48 | 56 | 72 | 60 | 100 | 95 | 97 | 100 |
| | II + III | | | | | | | | | |
| Galium aparine | 60 | 95 | 57 | 62 | 87 | 80 | 100 | 100 | 98 | 100 |
| Raphanus raphanistrum | 67 | 80 | 59 | 65 | 78 | 75 | 100 | 100 | 95 | 100 |
| Stellaria media | 60 | 78 | 87 | 60 | 80 | 73 | 100 | 100 | 96 | 100 |

0 = no damage
100 = complete destruction

EXAMPLE 2

In the open, various plants were treated at a growth height of from 2 to 10 cm with the following amounts of are;

I+V: 0.25+1.25, 1.25+0.25, 0.75+0.75 kg per hectare;

I+VI: 0.25+1.25, 1.25+0.25, 0.75+0.75 kg per hectare.

After 2 to 3 weeks it was ascertained that the compositions had a better herbicidal action than their components, combined with the same good crop plant compatibility.

The results are given below:

| kg/ha | 0.25 | 0.75 | 1.25 | 1.5 | 0.25 | 0.75 | 1.25 | 1.5 | 0.25 | 0.75 | 1.25 | 1.5 |
|---|---|---|---|---|---|---|---|---|---|---|---|---|
| Active ingredient | | I | | | | II | | | | III | | |
| Crop plants: | | | | | | | | | | | | |
| Festuca spp. | 0 | 0 | 0 | 0 | 0 | 0 | 0 | 0 | 0 | 0 | 0 | 0 |
| Lalium spp. | 0 | 0 | 0 | 0 | 0 | 0 | 0 | 0 | 0 | 0 | 0 | 0 |
| Poa spp. | 0 | 0 | 0 | 0 | 0 | 0 | 0 | 5 | 0 | 0 | 0 | 0 |
| | | IV | | | | V | | | | VI | | |
| Festuca spp. | 0 | 0 | 0 | 0 | 0 | 0 | 0 | 0 | 0 | 0 | 0 | 0 |
| Lalium spp. | 0 | 0 | 0 | 0 | 0 | 0 | 0 | 0 | 0 | 0 | 0 | 0 |
| Poa spp. | 0 | 0 | 0 | 0 | 0 | 0 | 0 | 0 | 0 | 0 | 0 | 0 |
| Unwanted plants: | | I | | | | II | | | | III | | |
| Ranunculus spp. | 10 | 15 | 20 | 25 | 25 | 40 | 50 | 60 | 15 | 32 | 45 | 50 |
| Rumex acetosa | 5 | 10 | 15 | 20 | 20 | 35 | 46 | 55 | 10 | 20 | 25 | 30 |
| | | IV | | | | V | | | | VI | | |
| Ranunculus spp. | 20 | 35 | 43 | 55 | 12 | 27 | 36 | 40 | 17 | 30 | 40 | 45 |
| Rumex acetosa | 15 | 30 | 35 | 43 | 10 | 25 | 32 | 40 | 15 | 29 | 42 | 48 |

| | kg/ha | | | | | | | | |
|---|---|---|---|---|---|---|---|---|---|
| | 0.25 + 1.25 | 1.25 + 0.25 | 0.75 + 0.75 | 0.25 + 1.25 | 1.25 + 0.25 | 0.75 + 0.75 | 0.25 + 1.25 | 1.25 + 0.25 | 0.75 + 0.75 |
| Active ingredient | | I + II | | | I + III | | | I + IV | |
| Crop plants: | | | | | | | | | |
| Festuca spp. | 0 | 0 | 0 | 0 | 0 | 0 | 0 | 0 | 0 |
| Lalium spp. | 0 | 0 | 0 | 0 | 0 | 0 | 0 | 0 | 0 |
| Poa spp. | 0 | 0 | 0 | 0 | 0 | 0 | 0 | 0 | 0 |
| Unwanted plants: | | | | | | | | | |
| Ranunculus spp. | 90 | 80 | 92 | 87 | 70 | 85 | 84 | 75 | 85 |
| Rumex acetosa | 86 | 70 | 78 | 64 | 60 | 67 | 75 | 63 | 77 |
| | | I + V | | | I + VI | | | | |
| Festuca spp. | 0 | 0 | 0 | 0 | 0 | 0 | | | |
| Lalium spp. | 0 | 0 | 0 | 0 | 0 | 0 | | | |
| Poa spp. | 0 | 0 | 0 | 0 | 0 | 0 | | | |
| Ranunculus spp. | 82 | 67 | 75 | 86 | 75 | 80 | | | |
| Rumex acetosa | 70 | 60 | 69 | 80 | 65 | 73 | | | |

0 = no damage
100 = complete destruction

EXAMPLE 3

In the open, various plants were treated at a growth height of from 2 to 22 cm with the following amounts of the following individual active ingredients and compositions thereof as anhydrous solutions:

I 3-isopropyl-2,1,3-benzothiadiazinone-(4)-2,2-dioxide, diethanolamine salt, 0.1, 0.25, 0.5, 0.75, 1, 2 and 3 kg per hectare;

II 3-isopropyl-2,1,3-benzothiadiazinone-(4)-2,2-dioxide, dimethylamine salt, 0.1, 0.25, 0.5, 0.75, 1, 2 and 3 kg per hectare;

III γ-(2,4-dichlorophenoxy)-butyric acid, dimethylamine salt, 0.1, 0.25, 0.5, 0.75, 1, 2 and 3 kg per hectare;

IV γ-(2,4-dichlorophenoxy)-butyric acid, diethanolamine salt, 0.1, 0.25, 0.5, 0.75, 1, 2 and 3 kg per hectare;

V α-(2-methylphenoxy)-propionic acid, dimethylamine salt, 0.1, 0.25, 0.5, 0.75, 1, 2 and 3 kg per hectare; for comparison, VI N-p-chlorophenyl-N',N'-dimethylurea, 2 and 3 kg per hectare;

I+III: 0.1+1, 1+0.1, 0.25+0.25, 0.25+0.75, 0.75+0.25, 0.5+0.5, 2+1, 1+2, 1+1 kg per hectare;

I+IV: 0.1+1, 1+0.1, 0.25+0.25, 0.25+0.75, 0.75+0.25, 0.5+0.5, 2+1, 1+2, 1+1 kg per hectare;

I+V: 0.1+1, 1+0.1, 0.25+0.25, 0.25+0.75, 0.75+0.25, 0.5+0.5, 2+1, 1+2, 1+1 kg per hectare;

II+III: 0.1+1, 1+0.1, 0.25+0.25, 0.25+0.75, 0.75+0.25, 0.5+0.5, 2+1, 1+2, 1+1 kg per hectare;

II+V: 0.1+1, 1+0.1, 0.25+0.25, 0.25+0.75, 0.75+0.25, 0.5+0.5, 2+1, 1+2, 1+1 kg per hectare;

VI+I: 2+1 kg per hectare.

After 2 to 3 weeks it was ascertained that the compositions of the invention had better crop plant compatibility and a better herbicidal action than individual active ingredients I to VI and composition VI+I.

The results are given below:

| kg/ha | 0.1 | 0.25 | 0.5 | 0.75 | 1 | 2 | 3 | 0.1 | 0.25 | 0.5 | 0.75 | 1 | 2 | 3 |
|---|---|---|---|---|---|---|---|---|---|---|---|---|---|---|
| Active ingredient | | | I | | | | | | | | II | | | |
| Crop plants: | | | | | | | | | | | | | | |
| *Triticum aestivum* | 0 | 0 | 0 | 0 | 0 | 0 | 0 | 0 | 0 | 0 | 0 | 0 | 0 | 0 |
| *Hordeum vulgare* | 0 | 0 | 0 | 0 | 0 | 0 | 0 | 0 | 0 | 0 | 0 | 0 | 0 | 0 |
| Unwanted plants: | | | | | | | | | | | | | | |
| *Galium aparine* | 15 | 25 | 35 | 45 | 65 | 80 | 95 | 10 | 20 | 30 | 40 | 50 | 75 | 100 |
| *Lamium amplexicaule* | 0 | 6 | 10 | 25 | 35 | 60 | 75 | 0 | 5 | 10 | 20 | 40 | 50 | 60 |
| *Raphanus raphanistrum* | 10 | 20 | 35 | 43 | 60 | 80 | 100 | 8 | 17 | 30 | 35 | 55 | 75 | 100 |
| *Stellaria media* | 5 | 10 | 20 | 40 | 60 | 90 | 100 | 5 | 10 | 20 | 35 | 50 | 75 | 95 |
| | | | III | | | | | | | | IV | | | |

-continued

| | | | | | | | | | | | | | | |
|---|---|---|---|---|---|---|---|---|---|---|---|---|---|---|
| *Triticum aestivum* | 0 | 0 | 0 | 0 | 0 | 0 | 5 | 0 | 0 | 0 | 0 | 0 | 0 | 5 |
| *Hordeum vulgare* | 0 | 0 | 0 | 0 | 0 | 0 | 5 | 0 | 0 | 0 | 0 | 0 | 0 | 5 |
| *Galium aparine* | 5 | 9 | 12 | 15 | 18 | 30 | 48 | 5 | 10 | 12 | 15 | 18 | 30 | 50 |
| *Lamium amplexicaule* | 5 | 10 | 15 | 20 | 25 | 40 | 65 | 7 | 15 | 20 | 30 | 35 | 55 | 75 |
| *Raphanus raphanistrum* | 2 | 5 | 11 | 15 | 18 | 30 | 60 | 4 | 7 | 10 | 15 | 18 | 35 | 60 |
| *Stellaria media* | 0 | 2 | 5 | 6 | 8 | 20 | 30 | 0 | 3 | 5 | 5 | 7 | 25 | 35 |
| Active ingredient | | | | V | | | | | | | VI | | | |
| Crop plants: | | | | | | | | | | | | | | |
| *Triticum aestivum* | 0 | 0 | 0 | 0 | 0 | 0 | 5 | | | | | | 90 | 100 |
| *Hordeum vulgare* | 0 | 0 | 0 | 0 | 0 | 0 | 7 | | | | | | 95 | 100 |
| Unwanted plants: | | | | | | | | | | | | | | |
| *Galium aparine* | 0 | 5 | 10 | 15 | 18 | 32 | 42 | | | | | | 90 | 100 |
| *Lamium amplexicaule* | 7 | 10 | 18 | 25 | 35 | 56 | 80 | | | | | | 100 | 100 |
| *Raphanus raphanistrum* | 2 | 4 | 10 | 12 | 16 | 35 | 65 | | | | | | 100 | 100 |
| *Stellaria media* | 0 | 3 | 5 | 7 | 9 | 24 | 35 | | | | | | 100 | 100 |
| kg/ha | 0.1 + 1 | 1 + 0.1 | 0.25 + 0.25 | 0.25 + 0.75 | 0.75 + 0.25 | 0.5 + 0.5 | 2 + 1 | 1 + 2 | 1 + 1 | 2 + 1 | | | | |
| Active ingredient | | | | | I + III | | | | | | | | | |
| Crop plants: | | | | | | | | | | | | | | |
| *Triticum acestivum* | 0 | 0 | 0 | 0 | 0 | 0 | 0 | 0 | 0 | | | | | |
| *Hordeum vulgare* | 0 | 0 | 0 | 0 | 0 | 0 | 0 | 0 | 0 | | | | | |
| Unwanted plants: | | | | | | | | | | | | | | |
| *Galium aparine* | 78 | 100 | 70 | 82 | 90 | 86 | 100 | 100 | 96 | | | | | |
| *Lamium amplexicaule* | 75 | 80 | 58 | 77 | 74 | 70 | 100 | 98 | 87 | | | | | |
| *Raphanus raphanistrum* | 67 | 97 | 60 | 70 | 83 | 79 | 100 | 100 | 98 | | | | | |
| *Stellaria media* | 58 | 90 | 52 | 60 | 80 | 68 | 100 | 100 | 100 | | | | | |
| | | | | | I + IV | | | | | | | | | |
| *Triticum aestivum* | 0 | 0 | 0 | 0 | 0 | 0 | 0 | 0 | 0 | | | | | |
| *Hordeum vulgare* | 0 | 0 | 0 | 0 | 0 | 0 | 0 | 0 | 0 | | | | | |
| *Galium aparine* | 75 | 100 | 69 | 73 | 90 | 86 | 100 | 100 | 100 | | | | | |
| *Lamium amplexicaule* | 80 | 79 | 56 | 80 | 74 | 70 | 100 | 100 | 97 | | | | | |
| *Raphanus raphanistrum* | 70 | 95 | 60 | 73 | 87 | 84 | 100 | 100 | 100 | | | | | |
| *Stellaria media* | 61 | 92 | 52 | 60 | 80 | 65 | 100 | 100 | 96 | | | | | |
| Active ingredient | | | | | I + V | | | | | | | | | |
| *Triticum aestivum* | 0 | 0 | 0 | 0 | 0 | 0 | 0 | 0 | 0 | | | | | |
| *Hordeum vulgare* | 0 | 0 | 0 | 0 | 0 | 0 | 0 | 0 | 0 | | | | | |
| *Galium aparine* | 75 | 92 | 68 | 76 | 87 | 80 | 100 | 100 | 100 | | | | | |
| *Lamium amplexicaule* | 70 | 74 | 50 | 67 | 70 | 65 | 100 | 100 | 98 | | | | | |
| *Raphanus raphanistrum* | 67 | 98 | 60 | 72 | 80 | 82 | 100 | 100 | 100 | | | | | |
| *Stellaria media* | 58 | 90 | 47 | 61 | 75 | 66 | 100 | 100 | 100 | | | | | |
| | | | | | II + III | | | | | | | | | |
| *Triticum aestivum* | 0 | 0 | 0 | 0 | 0 | 0 | 0 | 0 | 0 | | | | | |
| *Hordeum vulgare* | 0 | 0 | 0 | 0 | 0 | 0 | 0 | 0 | 0 | | | | | |
| *Galium aparine* | 65 | 80 | 62 | 70 | 82 | 76 | 100 | 100 | 96 | | | | | |
| *Lamium amplexicaule* | 70 | 82 | 51 | 67 | 70 | 65 | 100 | 100 | 95 | | | | | |
| *Raphanus raphanistrum* | 60 | 90 | 55 | 60 | 78 | 77 | 100 | 100 | 100 | | | | | |
| *Stellaria media* | 51 | 86 | 47 | 53 | 75 | 60 | 100 | 100 | 92 | | | | | |
| Active ingredient | | | | | II + V | | | | | | VI + I | | | |
| *Triticum aestivum* | 0 | 0 | 0 | 0 | 0 | 0 | 0 | 0 | 0 | 90 | | | | |
| *Hordeum vulgare* | 0 | 0 | 0 | 0 | 0 | 0 | 0 | 0 | 0 | 95 | | | | |
| *Galium aparine* | 63 | 80 | 60 | 72 | 82 | 75 | 100 | 100 | 96 | 100 | | | | |
| *Lamium amplexicaule* | 70 | 83 | 48 | 67 | 70 | 63 | 100 | 100 | 97 | 100 | | | | |
| *Raphanus raphanistrum* | 66 | 90 | 60 | 63 | 82 | 76 | 100 | 100 | 100 | 100 | | | | |
| *Stellaria media* | 47 | 87 | 49 | 55 | 75 | 60 | 100 | 98 | 100 | 100 | | | | |

0 = no damage
100 = complete destruction

EXAMPLE 4

In the open, various plants were treated at a growth height of from 3 to 25 cm with the following amounts of the following individual active ingredients and compositions thereof as oil dispersions:

I  3-isopropyl-2,1,3-benzothiadiazinone-(4)-2,2-dioxide, 0.25, 0.5, 0.75 and 1 kg per hectare;

II γ-(2,4-dichlorophenoxy)-butyric acid, isooctyl ester, 0.25, 0.5, 0.75 and 1 kg per hectare;

II α-(2-methylphenoxy)-propionic acid, isooctyl ester, 0.25, 0.5, 0.75 and 1 kg per hectare;

I+II 0.25+0.25, 0.25+0.75, 0.75+0.25 kg per hectare;
I+III 0.25+0.25, 0.25+0.75, 0.75+0.25 kg per hectare.

After 12 to 17 days it was ascertained that the compositions had a better herbicidal action than their components, combined with the same good crop plant compatibility.

The results are given below:

| | Active ingredient | | | | | | | | | | | |
|---|---|---|---|---|---|---|---|---|---|---|---|---|
| | I | | | | II | | | | III | | | |
| kg/ha | 0.25 | 0.5 | 0.75 | 1 | 0.25 | 0.5 | 0.75 | 1 | 0.25 | 0.5 | 0.75 | 1 |
| Crop plants: | | | | | | | | | | | | |
| *Triticum aestivum* | 0 | 0 | 0 | 0 | 0 | 0 | 0 | 0 | 0 | 0 | 0 | 0 |
| *Hordeum vulgare* | 0 | 0 | 0 | 0 | 0 | 0 | 0 | 0 | 0 | 0 | 0 | 0 |

-continued

| Unwanted plants: | | | | | | | | | | | | |
|---|---|---|---|---|---|---|---|---|---|---|---|---|
| *Galium aparine* | 20 | 30 | 40 | 50 | 9 | 12 | 15 | 18 | 5 | 10 | 15 | 18 |
| *Lamium amplexicaule* | 5 | 10 | 20 | 40 | 10 | 15 | 20 | 25 | 10 | 18 | 25 | 35 |

| | Active ingredient | | | | | |
|---|---|---|---|---|---|---|
| | I + II | | | I + III | | |
| kg/ha | 0.25 + 0.25 | 0.25 + 0.75 | 0.75 + 0.25 | 0.25 + 0.25 | 0.25 + 0.75 | 0.75 + 0.25 |
| *Triticum aestivum* | 0 | 0 | 0 | 0 | 0 | 0 |
| *Hordeum vulgare* | 0 | 0 | 0 | 0 | 0 | 0 |
| *Galium aparine* | 62 | 70 | 82 | 60 | 72 | 82 |
| *Lamium amplexicaule* | 51 | 67 | 70 | 48 | 67 | 70 |

0 = no damage
100 = complete destruction

EXAMPLE 5

In the open, various plants were treated at a growth height of from 0.5 to 12 cm with the following amounts of the following individual active ingredients and compositions thereof as granules:

I 3-isopropyl-2,1,3-benzothiadiazinone-(4)-2,2-dioxide, 0.5, 0.75, 1 and 1.5 kg per hectare;
II γ-(2-methyl-4-chlorophenoxy)-butyric acid, 0.5, 0.75, 1 and 1.5 kg per hectare;
I+II: 0.5+1, 1+0.5, 0.75+0.75 kg per hectare.

After 2 to 3 weeks it was ascertained that the compositions had a better herbicidal action than their components, combined with the same good crop plant compatibility.

The results are given below:

EXAMPLE 6

In the open, various plants were treated at a growth height of from 3 to 26 cm with the following amounts of the following individual active ingredients and compositions thereof as directly sprayable solutions:

I 3-isopropyl-2,1,3-benzothiadiazinone-(4)-2,2-dioxide, diethanolamine salt, 0.5, 1, 1.5 and 2 kg per hectare;
II γ-(2,4-dichlorophenoxy)-butyric acid, isooctyl ester, 0.5, 1, 1.5 and 2 kg per hectare;
III α-(2-methylphenoxy)-propionic acid, isooctyl ester, 0.5, 1, 1.5 and 2 kg per hectare;
I+II: 0.5+1.5 1.5+0.5, 1+1 kg per hectare;
I+III: 0.5+1.5, 1.5+0.5, 1+1 kg per hectare.

After 2 to 3 weeks it was ascertained that the compositions had a better herbicidal action than their components, combined with the same good crop plant compatibility.

The results are given below:

| | Active ingredient | | | | | | | | | | | |
|---|---|---|---|---|---|---|---|---|---|---|---|---|
| | I | | | | II | | | | III | | | |
| kg/ha | 0.5 | 1 | 1.5 | 2 | 0.5 | 1 | 1.5 | 2 | 0.5 | 1 | 1.5 | 2 |
| Crop plants: | | | | | | | | | | | | |
| *Triticum aestivum* | 0 | 0 | 0 | 0 | 0 | 0 | 0 | 0 | 0 | 0 | 0 | 0 |
| *Hordeum vulgare* | 0 | 0 | 0 | 0 | 0 | 0 | 0 | 0 | 0 | 0 | 0 | 0 |
| Unwanted plants: | | | | | | | | | | | | |
| *Galium aparine* | 25 | 67 | 70 | 78 | 15 | 20 | 26 | 35 | 12 | 20 | 25 | 35 |
| *Lamium amplexicaule* | 10 | 36 | 48 | 64 | 17 | 30 | 37 | 45 | 20 | 35 | 46 | 60 |

| | Active ingredient | | | | | |
|---|---|---|---|---|---|---|
| | I + II | | | I + III | | |
| kg/ha | 0.5 + 1.5 | 1.5 + 0.5 | 1 + 1 | 0.5 + 1.5 | 1.5 + 0.5 | 1 + 1 |
| *Triticum aestivum* | 0 | 0 | 0 | 0 | 0 | 0 |
| *Hordeum vulgare* | 0 | 0 | 0 | 0 | 0 | 0 |
| *Galium aparine* | 87 | 100 | 100 | 85 | 100 | 100 |
| *Lamium amplexicaule* | 80 | 95 | 94 | 90 | 95 | 98 |

0 = no damage
100 = complete destruction

| | Active ingredient | | | | | | | | | |
|---|---|---|---|---|---|---|---|---|---|---|
| | I | | | | II | | | | I + II | | |
| kg/ha | 0.5 | 0.75 | 1 | 1.5 | 0.5 | 0.75 | 1 | 1.5 | 0.5 + 1 | 1 + 0.5 | 0.75 + 0.75 |
| Crop plants: | | | | | | | | | | | |
| *Medicago sativa* | 0 | 0 | 0 | 0 | 0 | 0 | 0 | 0 | 0 | 0 | 0 |
| *Pisum sativum* | 0 | 0 | 0 | 0 | 0 | 0 | 0 | 0 | 0 | 0 | 0 |
| Unwanted plants: | | | | | | | | | | | |
| *Galium aparine* | 20 | 30 | 45 | 65 | 5 | 10 | 15 | 20 | 70 | 87 | 76 |
| *Stellaria media* | 20 | 35 | 50 | 65 | 5 | 10 | 14 | 22 | 73 | 90 | 82 |

0 = no damage
100 = complete destruction

EXAMPLE 7

The herbicidal action of the composition of 3-isopropyl-2,1,3-benzothiadiazinone-(4)-2,2-dioxide and γ-(2,4-dichlorophenoxy)-butyric acid was compared to that of the mixture of 3-isopropyl-2,1,3-benzothiadiazinone dioxide (bentazon) and γ-(b 2-methyl-4-chlorophenoxy)-propionic acid (mecoprop; MCPP), the individual components being as follows:

I—3-isopropyl-2,1,3-benzothiadiazinone-(4)-2,2-dioxide
II—γ-(2-methyl-4-chlorophenoxy)-propionic acid, dimethylamine salt
III—γ-(2,4-dichlorophenoxy)-butyric acid, dimethylamine salt.

In these experiments, the test plants were grown to a height of 5 to 12 cm in plastic flowerpots having a volume of 300 cm³ and filled with a sandy loam, and were then treated with mixtures I+II and I+III. The mixtures were sprayed, as emulsions or suspensions in water, through finely distributing nozzles in a closed cabinet.

The test plants were then placed, depending on their temperature requirements, in warmer or cooler sections of the greenhouse. The experiments were run for from 3 to 4 weeks. During this period the plants were tended and their reaction to the various herbicide treatments was assessed.

The application rates are given in kg of active ingredient per hectare. The results are given on a 0 to 100 scale, 0 denoting no damage or normal growth, and 100 denoting complete destruction. The crop plants used in the experiments were *Arachis hypogaea* (peanuts), Glycine max (soybeans), *Pisum sativum* (English peas), *Trifolium pratense* (red clover), and *Triticum aestivum* (wheat) and the unwanted plants were *Sida spinosa* (prickly sida; tea weed), *Xanthium pensylvanicum* (cocklebur), *Galium aparine* (catchweed bedstraw) and *Stellaria media* (chickweed).

Experiment A

Mixtures I+II and I+III were used in varying component ratios and at different application rates for combatting *Galium aparine* and *Stellaria media* in *Triticum aestivum*. The results are given in the following table.

| Active ingredient mixture | Appln. rate kg/ha | Damage to test plants | | |
|---|---|---|---|---|
| | | Triticum aestivum | Galium aparine | Stellaria media |
| I + II | 0.25 + 0.25 | 7 | 98 | 100 |
| | 0.5 + 0.5 | 17 | 98 | 100 |
| | 0.75 + 0.75 | 8 | 98 | 100 |
| | 1.0 + 1.0 | 20 | 98 | 100 |
| | 2.0 + 2.0 | 25 | 98 | 100 |
| | 0.125 + 0.25 | 10 | 65 | 90 |
| | 0.25 + 0.75 | 8 | 90 | 100 |
| | 0.25 + 1.25 | 17 | 85 | 100 |
| | 0.25 + 1.75 | 18 | 98 | 100 |
| | 0.125 + 1.375 | 7 | 98 | 85 |

-continued

| Active ingredient mixture | Appln. rate kg/ha | Damage to test plants | | |
|---|---|---|---|---|
| | | Triticum aestivum | Galium aparine | Stellaria media |
| | 0.375 + 0.125 | 3 | 85 | 100 |
| | 0.75 + 0.25 | 3 | 98 | 100 |
| | 1.25 + 0.25 | 0 | 98 | 100 |
| | 1.75 + 0.25 | 3 | 95 | 100 |
| | 1.375 + 0.125 | 5 | 80 | 100 |
| I + III | 0.25 + 0.25 | 0 | 40 | 98 |
| | 0.5 + 0.5 | 3 | 70 | 100 |
| | 1.0 + 1.0 | 7 | 80 | 100 |
| | 0.125 + 0.25 | 7 | 10 | 70 |
| | 0.125 + 1.375 | 8 | 50 | 85 |
| | 0.375 + 0.125 | 0 | 30 | 90 |

0 = no damage,
100 = plants completely destroyed

These figures clearly show that the crop plant wheat is damaged by the mixture of I+II but not by the mixture of I+III.

Experiment B

Mixtures I+II and I+III were used in varying component ratios and at different application rates for combatting unwanted plants in leguminosae such as *Arachis hypogaea*, Glycine max, *Pisum sativum* and *Trifolium pratense*. The results are given in the following table:

| Active ingredient mixture | Appln. rate kg/ha | Damage to test plants | | | | | |
|---|---|---|---|---|---|---|---|
| | | Arachis hypogaea | Glycine max | Pisum sativum | Trifolium pratense | Sida spinosa | Xanthium pensylvanicum |
| I + II | 0.25 + 0.25 | 5 | 20 | 70 | 63 | 98 | 100 |
| | 0.5 + 0.5 | 5 | 50 | 90 | 82 | 100 | 100 |
| | 1.0 + 1.0 | 28 | 100 | 100 | 98 | 100 | 100 |
| | 0.125 + 1.375 | 45 | 100 | 98 | 95 | 58 | 100 |
| | 0.125 + 0.25 | 10 | 29 | 80 | 18 | 20 | 32 |
| | 0.25 + 1.25 | 45 | 100 | 100 | 93 | 95 | 100 |
| I + III | 0.25 + 0.25 | 0 | 0 | 5 | 0 | 88 | 100 |
| | 0.5 + 0.5 | 0 | 10 | 10 | 0 | 98 | 100 |
| | 1.0 + 1.0 | 0 | 16 | 20 | 3 | 100 | 100 |
| | 0.125 + 1.375 | 0 | 15 | 10 | 0 | 78 | 100 |
| | 0.125 + 0.25 | 0 | 10 | 10 | 0 | 95 | 100 |

0 = no damage,
100 = plants completely destroyed

These results show that the mixture of I+III is excellently tolerated both by cereals and leguminosae, whereas the prior art mixture of I+II damage cereals and almost completely destroys leguminosae at application rates necessary for effectively combatting weeds; consequently, the latter mixture rules itself out for use in leguminous crops. The herbicidal action on *Sida spinosa* and *Xanthium pensylvanicum* remains excellent when the phenoxypropionic acid derivative in the mixture is replaced by the phenoxybutyric acid derivative.

It will therefore be apparent from Experiments A and B that the mixture of I+III has the advantage over the prior art mixture of I+II that it may be used not only in cereals but also in leguminosae. This unexpected discovery is of considerable importance in practice, because cereals are often used as nurse crops for undersown legumes. The legumes, e.g *Trifolium pratense*, are sown when the cereal has already developed several leaves, and they germinate and grow in the protection of the cereal and have already formed a new cover when the cereal is harvested. It will therefore be clear that only those herbicides can be used in undersown legumes which are tolerated by both crop plants, cereals and legumes, and which simultaneously have the requisite herbicidal action on unwanted plants.

EXAMPLE 8

The herbicidal action of the composition of 3-isopropyl-2,1,3-benzothiadiazinone-(4)-2,2-dioxide and γ-(2,4-dichlorophenoxy)-butyric acid was compared to that of the mixture of 3-isopropyl-2,1,3-benzothiadiazinone dioxide (bentazon) and α-(2,4-dichlorophenoxy)-propionic acid (dicloroprop), the individual components being as follows:

A—3-isopropyl-2,1,3-benzothiadiazinone-(4)-2,2-dioxide

B—α-(2,4-dichlorophenoxy)-propionic acid, dimethylamine salt

C—γ-(2,4-dichlorophenoxy)-butyric acid, dimethylamine salt

In these experiments, the test plants were grown to a height of 5 to 12 cm in plastic flowerpots having a volume of 300 cm$^3$ and filled with a sandy loam, and were then treated with mixtures A+B and A+C. The mixtures were sprayed, as emulsions or suspensions in water, through finely distributing nozzles in a closed cabinet.

The test plants were then placed, depending on their temperature requirements, in warmer or cooler sections of the greenhouse. The experiments were run for from 3 to 4 weeks. During this period the plants were tended and their reaction to the various herbicide treatments was assessed.

The application rates are given in kg of active ingredient per hectare. The results are given on a 0 to 100 scale, 0 denoting no damage or normal growth, and 100 denoting complete destruction.

The test plants used in the experiments were *Arachis hypogaea* (peanuts), *Glycine max* (soybeans), *Pisum sativum* (English peas), *Trifolium pratense* (red clover), and *Triticum aestivum* (wheat) and the unwanted plant was *Ipomoea* spp. (morning glory).

The results are given in the Table below:

These results show that the mixture of A+C is much better tolerated by leguminosae at application rates necessary for effective control of unwanted plants than is the mixture of A+B. Cereals, as exemplified by wheat, tolerate the mixtures equally well. The superiority of the mixture of A+C thus resides in the fact that it may, in contrast to the mixture of A+B, be used not only in cereals but also in leguminosae; this is of considerable practical importance for the control of unwanted plants in cereal crops which are undersown with legumes.

Furthermore, these results show that the herbicidal action of the mixture A+C on Ipomoea is superior to that of the prior art mixture A+B, especially at the lower application rates.

We claim:

1. A herbicide composition comprising a carrier having dispersed therein a herbicidally effective amount of a mixture of herbicides consisting essentially of
   (a) 3-isopropyl-2,1,3-benzothiadiazinone-(4)-2,2-dioxide or a salt thereof, and
   (b) γ-(2,4-dichlorophenoxy)-butyric acid or a salt or ester thereof in a weight ratio of a to b in the range of 10:1 to 1:10.

2. The herbicide composition of claim 1, wherein said salt of compound (a) is the ammonium, sodium, potassium, calcium, magnesium, ethylamine, dimethylamine, diethylamine, ethanolamine, diethanolamine or dimethyl-ethanolamine salt.

3. The herbicide composition of claim 2, wherein compound (b) is said butyric acid or the sodium, diethanolamine or dimethyl amine salt thereof.

4. The herbicide composition of claim 1, wherein compound (b) is γ-(2,4-dichlorophenoxy)-butyric acid.

5. The herbicide composition of claim 1 or claim 4, wherein compound (a) is 3-isopropyl-2,1,3-benzothiadiazinone-(4)-2,2-dioxide.

6. The herbicide composition of claim 5, wherein the weight ratio of (a) to (b) is from 3:1 to 1:3.

| Active ingredient mixture | Appln. rate kg/ha | Damage to test plants | | | | | |
|---|---|---|---|---|---|---|---|
| | | *Arachis hypogaea* | *Glycine max.* | *Pisum Sativum* | *Trifolium pratense* | *Triticum aestivum* | *Ipomoea* spp. |
| A + B | 0.25 + 0.25 | 9 | 9 | 34 | 31 | 0 | 48 |
| | 0.5 + 0.5 | 13 | 12 | 86 | 54 | 0 | 66 |
| | 1.0 + 1.0 | 16 | 19 | 94 | 72 | 8 | 98 |
| | 2.0 + 2.0 | 25 | 35 | 100 | 84 | 25 | 100 |
| A + C | 0.25 + 0.25 | 7 | 8 | 5 | 8 | 0 | 71 |
| | 0.5 + 0.5 | 7 | 13 | 9 | 14 | 0 | 98 |
| | 1.0 + 1.0 | 7 | 15 | 15 | 18 | 8 | 100 |
| | 2.0 + 2.0 | 6 | 19 | 20 | 15 | 25 | 100 |